United States Patent
Bai et al.

(10) Patent No.: US 11,638,912 B2
(45) Date of Patent: May 2, 2023

(54) METAL CATALYST SYNTHESIS AND ACID/METAL BIFUNCTIONAL CATALYST SYSTEMS THEREOF

(71) Applicant: ExxonMobil Technology and Engineering Company, Annandale, NJ (US)

(72) Inventors: Chuansheng Bai, Phillipsburg, NJ (US); Majosefina Cunningham, Whitehall, PA (US); Jihad M. Daaka, Whitehouse Station, NJ (US); Preeti Kamakoti, Berkeley Heights, NJ (US); Aruna Ramkrishnan, Bridgewater, NJ (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 218 days.

(21) Appl. No.: 16/947,699

(22) Filed: Aug. 13, 2020

(65) Prior Publication Data

US 2021/0046460 A1     Feb. 18, 2021

Related U.S. Application Data

(60) Provisional application No. 62/886,984, filed on Aug. 15, 2019.

(51) Int. Cl.
   *B01J 23/80*     (2006.01)
   *C07C 41/01*     (2006.01)
   (Continued)

(52) U.S. Cl.
   CPC ........... *B01J 23/80* (2013.01); *B01J 35/0013* (2013.01); *B01J 35/026* (2013.01);
   (Continued)

(58) Field of Classification Search
   CPC ...... B01J 23/80; B01J 35/0013; B01J 35/023; B01J 35/026; B01J 35/1014;
   (Continued)

(56) References Cited

U.S. PATENT DOCUMENTS

4,423,155 A    12/1983 Bell et al.
5,218,003 A     6/1993 Lewnard et al.
(Continued)

FOREIGN PATENT DOCUMENTS

| | | |
|---|---|---|
| CN | 101485983 A | 7/2009 |
| CN | 104646049 A | 5/2015 |

(Continued)

OTHER PUBLICATIONS

Bae, J.-W., et al., "Coproduction of Methanol and Dimethyl Ether from Biomass-Derived Syngas on a Cu—ZnO—Al2O3/ γ-Al2O3 Hybrid Catalyst", Energy and Fuels, vol. 22, No. 1, pp. 223-230 (2008).

(Continued)

*Primary Examiner* — Patricia L. Hailey (74) *Attorney, Agent, or Firm* — Shook, Hardy & Bacon L.L.P.

(57) ABSTRACT

Methods of producing metal catalysts can include mixing two or more metal salts and an aluminum salt in water to produce a metal catalyst precursor solution having a pH of about 2.5 to about 4.0; mixing the metal catalyst precursor solution and a basic solution having a pH of about 10 to about 13 to produce a mixture with a pH of about 6 to about 7 and a precipitate; producing a powder from the precipitate; and calcining the powder to produce a metal catalyst. Such metal catalysts may be useful in producing bifunctional catalyst systems that are useful in, among other things, converting syngas to dimethyl ether in a single reactor.

22 Claims, 6 Drawing Sheets

(51) Int. Cl.
| | |
|---|---|
| *B01J 37/03* | (2006.01) |
| *B01J 37/08* | (2006.01) |
| *B01J 37/06* | (2006.01) |
| *B01J 37/02* | (2006.01) |
| *B01J 37/00* | (2006.01) |
| *B01J 37/18* | (2006.01) |
| *B01J 35/02* | (2006.01) |
| *B01J 35/00* | (2006.01) |
| *B01J 35/10* | (2006.01) |
| *B01J 37/04* | (2006.01) |

(52) U.S. Cl.
CPC ....... *B01J 35/1014* (2013.01); *B01J 35/1019* (2013.01); *B01J 35/1038* (2013.01); *B01J 35/1066* (2013.01); *B01J 37/0018* (2013.01); *B01J 37/0036* (2013.01); *B01J 37/0236* (2013.01); *B01J 37/031* (2013.01); *B01J 37/04* (2013.01); *B01J 37/06* (2013.01); *B01J 37/088* (2013.01); *B01J 37/18* (2013.01); *C07C 41/01* (2013.01)

(58) Field of Classification Search
CPC ................ B01J 35/1019; B01J 35/1038; B01J 35/1066; B01J 37/0018; B01J 37/0036; B01J 37/0236; B01J 37/031; B01J 37/04; B01J 37/06; B01J 37/088; B01J 37/18; C01P 2004/61; C01P 2004/90; C01P 2006/14; C01P 2066/16; C01P 2006/16; C07C 41/01
USPC ....... 502/104, 302, 305, 308, 312, 313, 317, 502/320, 323–327, 330, 332, 346, 348, 502/351, 355
See application file for complete search history.

(56) References Cited

U.S. PATENT DOCUMENTS

| | | | |
|---|---|---|---|
| 6,069,107 A | | 5/2000 | Kuznetsov et al. |
| 2012/0157554 A1 | | 6/2012 | Okuyama et al. |
| 2013/0030224 A1 | * | 1/2013 | Kim ........................ B01J 23/74 |
| | | | 568/885 |
| 2013/0211147 A1 | | 8/2013 | Cheiky et al. |
| 2016/0347906 A1 | | 12/2016 | Williams et al. |
| 2017/0297986 A1 | | 10/2017 | Lee et al. |

FOREIGN PATENT DOCUMENTS

| | | | | |
|---|---|---|---|---|
| CN | 1044646049 | * | 5/2015 | ............. B01J 23/80 |
| CN | 104069856 B | | 4/2016 | |
| CN | 106536045 A | | 3/2017 | |
| JP | 2003-38957 A | | 2/2003 | |
| WO | WO 2005/046855 | * | 5/2005 | |

OTHER PUBLICATIONS

Kamata, H., et al., "Steam Reforming of Dimethyl Ether over Cu/ZnO/ZrO2 and γ-Al2O3 Mixed Catalyst Prepared by Extrusion", Journal of the Japan Petroleum Institute, vol. 51, No. 3, pp. 157-164 (2008).

Gentzen, M., et al., "Bifunctional catalysts based on colloidal Cu/Zn nanoparticles for the direct conversion of synthesis gas to dimethyl ether and hydrocarbons," Applied Catalysis A: General, vol. 557, pp. 99-107 (Year: 2018).

Gentzen, M., et al., "Bifunctional hybrid catalysts derived from Cu/Zn-based nanoparticles for single-step dimethyl ether synthesis", Catalysis Science & Technology, vol. 6, pp. 1-10 (2016).

Zhang, Q., et al., "Improvement of a Mesh-Type Cu/Ni/γ-Al2O3/Al Catalyst for Steam Reforming of Dimethyl Ether by Metal (Fe, Zn or La) Addition for CO in Situ Removal", Modem Research in Catalysis, vol. 7, pp. 1-16 (Jan. 31, 2018).

Non-Final Office Action dated Apr. 11, 2022 in U.S. Appl. No. 16/993,219, 12 pages.

Non-Final Office Action dated Aug. 4, 2022 in U.S. Appl. No. 16/947,704, 14 pages.

Non-Final Office Action dated Aug. 23, 2022 in U.S. Appl. No. 16/947,701, 10 pages.

Non-Final Office Action dated Sep. 15, 2022 in U.S. Appl. No. 16/947,706, 8 pages.

Notice of Allowance dated Oct. 21, 2022 in U.S. Appl. No. 16/993,219, 9 pages.

Final Office Action dated Jan. 12, 2023 in U.S. Appl. No. 16/947,704, 16 pages.

* cited by examiner

METAL CATALYST SYNTHESIS AND ACID/METAL BIFUNCTIONAL CATALYST SYSTEMS THEREOF

CROSS REFERENCE TO RELATED APPLICATIONS

This application claims priority to U.S. Provisional Application Ser. No. 62/886,984 filed Aug. 15, 2019, which is herein incorporated by reference in its entirety.

FIELD

The present disclosure relates to catalysts for direct conversion of syngas to dimethyl ether.

BACKGROUND

Various processes have been proposed for producing dimethyl ether from natural gas. One such process involves co-feeding natural gas with an enriched oxygen stream to an autothermal reformer to produce syngas. Dimethyl ether may then be produced in a two-stage process. In a first stage, methanol is synthesized from the syngas. In the methanol synthesis step, un-reacted gas from the methanol synthesis reactor may be recycled back to the reactor, thereby acting as a syngas quench cooler. The recycle ratio (recycle gas to syngas feed gas) can be quite high in commercial practice, such as from 3:1 to 7:1, due to equilibrium limitations in methanol conversion. In the second stage, methanol is fed to a dimethyl ether reactor where dimethyl ether and water are produced. Water is separated from dimethyl ether in a subsequent stage.

Air separation (for providing an enriched oxygen feed), autothermal reforming, and substantial internal product recycle imposes significant operating and equipment costs for conventional systems for producing dimethyl ether from natural gas. It would therefore be desirable to provide new integrated processes for the production of dimethyl ether from natural gas.

A newer method has been developed for a one-stage process of converting syngas to dimethyl ether. The newer method uses two separate catalysts in a single reactor to convert CO and $H_2$ to methanol with a metal catalyst and the methanol to dimethyl ether with an acid second catalyst. However, the two catalysts being present together and mixed causes catalyst deactivation over time. For example, the acid catalysts produce coke that deactivates the metal catalysts. Further, the metal from the catalysts tends to migrate under reaction conditions preferentially to the acid sites of the acid catalysts and poison or deactivate the acid portion of the bifunctional catalyst.

SUMMARY

The present disclosure relates to methods of producing metal catalysts and bifunctional catalyst systems comprising said metal catalysts. The metal catalysts described herein are synthesized without buffer in a 1-step precipitation process, which produces a metal catalyst with reduced metal migration in the acid/metal bifunctional catalyst systems.

The present disclosure includes a method comprising: mixing two or more metal salts and an aluminum salt in water to produce a metal catalyst precursor solution having a pH of about 2.5 to about 4.0; mixing the metal catalyst precursor solution and a basic solution having a pH of about 10 to about 13 to produce a mixture with a pH of about 6 to about 7 and a precipitate; producing a powder from the precipitate; and calcining the powder to produce a metal catalyst.

The present disclosure also includes a metal catalyst produced according to the preceding method.

The present disclosure also includes an acid/metal bifunctional catalyst system comprising the metal catalyst produced according to the preceding method and an acid catalyst. Such acid/metal bifunctional catalyst systems can be prepared by dry mixing, extrusion methods, or slurry mixing.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present disclosure relates to methods of producing metal catalysts and bifunctional catalyst systems comprising said metal catalysts. The metal catalysts described herein are synthesized without buffer in a 1-step precipitation process, which produces a metal catalyst with reduced metal migration in the acid/metal bifunctional catalyst systems.

Metal Catalysts and Resultant Acid/Metal Bifunctional Catalyst Systems

The metal catalysts of the present disclosure are produced without using a buffer solution but rather monitoring the pH. Further, the metal salts and aluminum salt are in a single addition step, which produces a higher surface area, more amorphous sample that has less metal migration in acid/metal bifunctional catalyst systems.

Figure 1:
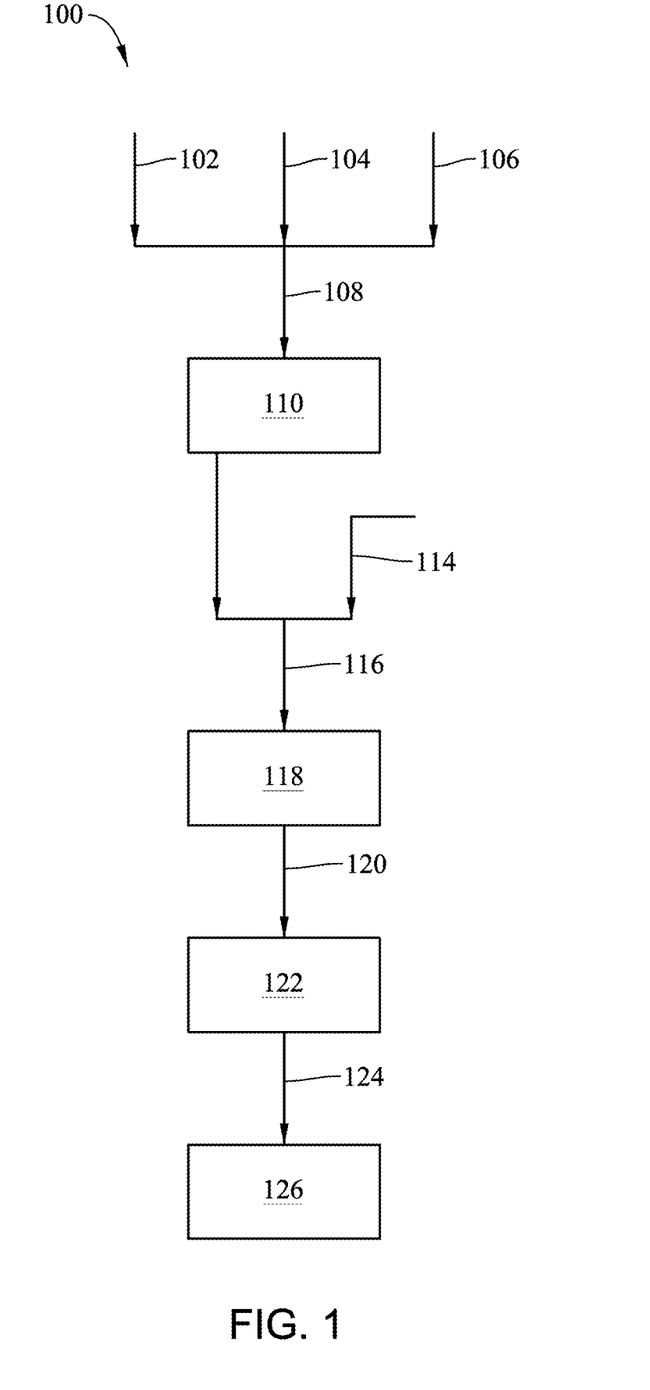
FIG. 1 is a flowchart illustrating an example method of preparing metal catalysts described herein with low alkali-metal concentrations.

FIG. 1 is a flowchart illustrating an example method 100 of preparing a metal catalyst. The method includes mixing 108 two or more metal salts (illustrated as first metal salt 102 and a second metal salt 104) and an aluminum salt 106 in water to produce a metal catalyst precursor solution 110. The salts 102, 104, 106 can, individually or in any combination, be dispersed in the water before mixing. Alternatively, one or more can be dispersed in the water and then the remaining salts can be added.

The method 100 then includes mixing 116 the metal catalyst precursor solution 110 with a basic solution 114, which produces a precipitate 118.

The first metal salt 102 can be a salt of a first metal selected from the group consisting of Cu, Cr, Ag, Au, Ru, Rh, Pd, Re, Os, Ir, and Pt, and a second metal salt 104 can be a salt of a second metal selected from the group consisting of Ti, V, Cr, Mn, Fe, Co, Ni, Zn, a rare earth metal, a La series metal, and a Y series metal. The metal catalyst precursor solution 110 can include one or more of the first metal salts 102 and one or more of the second metal salts 104.

The metal salts 102 and 104 and the aluminum salt 106 can be metal or aluminum salts with a counter ion selected from the group consisting of fluoride, chloride, bromide, acetate, carbonate, citrate, nitrate, nitrite, phosphate, sulfate, and the like. One skilled in the art will recognize the correct metal salts 102 and 104 and the aluminum salt 106 to use to cause a precipitate of the metals and aluminum to form.

The metal catalyst precursor solution 110 may have a pH of about 2.5 to about 4.0, or about 3 to about 3.5.

The basic solution 114 can have a pH about 10.0 to about 13.0 (or about 11.0 to about 12.5, or about 11.5 to about 12.5) and be capable of precipitating the metal catalyst precursor solution 110. Examples of basic solutions 114 include, but are not limited to, sodium carbonate, sodium hydroxide, ammonia hydroxide, ammonia carbonate, sodium hydrogen bicarbonate, and the carbonates, hydroxides, and hydrogen bicarbonates of alkali and alkaline metals. Combinations of bases can be used in making the basic solution 114.

Optionally, the metal catalyst precursor solution 110 and/or a basic solution 114 may be at an elevated temperature (e.g., about 40° C. to about 90° C., or about 50° C. to about 85° C., or about 60° C. to about 80° C.) before mixing.

The amount of each the metal catalyst precursor solution 110 with the basic solution 114 should be chosen to result in a mixture having a pH of about 6.0 to about 7.0, or about 6.3 to about 6.7. Preferably, the basic solution 114 is slowly added to the metal catalyst precursor solution 110 until the foregoing pH is achieved.

After reaching the prescribed pH, the mixture of the metal catalyst precursor solution 110 and a basic solution 114 may be aged at a room temperature or an elevated temperature (e.g., about 25° C. to about 90° C., or about 40° C. to about 85° C., or about 60° C. to about 80° C.) for a sufficient amount of time (e.g., 5 minutes to 24 hours, or 15 minutes to 12 hours, or 30 minutes to 6 hours) to produce a desired amount of the precipitate 118.

After the precipitate 118 is formed, the method 100 can include producing 120 a powder 122 from the precipitate 118. Producing 120 the powder 122 can include washing (e.g., with water), drying (e.g., at about 25° C. to about 90° C. for about 5 minutes to about 24 hours), and/or grinding the precipitate 118.

Once the powder 122 is produced, the method 100 includes calcining 124 the powder 122 to produce a metal catalyst 126. Calcining 124 may occur in an oxygen-containing gas (e.g., oxygen, air, oxygen-enriched air, and the like) at a temperature of about 200° C. to about 400° C. (or about 250° C. to about 350° C., or about 275° C. to about 375° C.) for any suitable amount of time (e.g., about 10 minutes to about 48 hours, or about 30 minutes to about 24 hours, or about 1 hour to about 12 hours, or about 1 hour to about 6 hours).

Preferably, the powder 122 comprises the water at about 5 wt % or less (or 0 wt % to about 5 wt %, or 0 wt % to about 3 wt %, or about 0.1 wt % to about 3 wt %, or 0 wt % to about 1 wt %).

The metal catalyst 126 should be suitable for converting CO and $H_2$ to methanol. Examples of metal catalysts 126 can include, but are not limited to, a M1/M2/Al catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different.

The metal catalyst 126 may have an average diameter (determined by light scattering) of about 0.01 μm to about 10 μm, or about 0.01 μm to about 1 μm, or about 0.1 μm to about 2 μm, or about 1 μm to about 5 μm, or about 2 μm to about 10 μm.

The metal catalyst 126 particles may have a $N_2$ BET surface area according to ASTM D3663-03 (2015) of about 40 $m^2$/g to about 200 $m^2$/g (about 50 $m^2$/g to about 175 $m^2$/g, or about 75 $m^2$/g to about 150 $m^2$/g, or about 100 $m^2$/g to about 140 $m^2$/g).

The metal catalyst 126 particles may have an average pore volume according to $N_2$ BET about 0.01 mL/g to about 0.1 mL/g (or about 0.02 mL/g to about 0.08 mL/g, or about 0.03 mL/g to about 0.06 mL/g).

The metal catalyst 126 particles may have an average pore size according to ASTM D4641-17 of about 15 nm to about 30 nm (or about 16 nm to about 25 nm, or about 17 nm to about 20 nm).

A metal catalyst described herein can then be wet or dry mixed with an acid catalyst and optionally inert particles to produce an acid/metal bifunctional catalyst system suitable for, among other things, converting syngas to dimethyl ether in a single reactor. Optionally, the mixture can further include binders and be extruded to form the acid/metal bifunctional catalyst system.

By way of nonlimiting example, an acid/metal bifunctional catalyst system can be formed by dry admixing a metal catalyst described herein, an acid catalyst, and optionally inert particles.

In another nonlimiting example, an acid/metal bifunctional catalyst system can be formed by mixing the metal catalyst described herein with an acid catalyst and a binder to form a dough; and extruding the dough to produce an acid/metal bifunctional catalyst system. Said acid/metal bifunctional catalyst system can be used as extruded or optionally dried (e.g., at about 25° C. to about 90° C. for about 5 minutes to about 24 hours), calcined (e.g., as described above), ground, or any combination thereof. Examples of binders include, but are not limited to, clay, theta-alumina, delta-alumina, alpha-alumina, silica, titania, zirconia, boric acid, carbon, organic compounds (e.g., polymers), and the like, and any combination thereof).

In another nonlimiting example, an acid/metal bifunctional catalyst system can be formed by mixing the metal catalyst described herein with an acid catalyst and a solvent to form a slurry; heating the slurry; and drying the slurry to produce an acid/metal bifunctional catalyst system. Said acid/metal bifunctional catalyst system can be used as extruded or optionally dried (e.g., at about 25° C. to about 90° C. for about 5 minutes to about 24 hours), calcined (e.g., as described above), ground, or any combination thereof. Examples of solvents include, but are not limited to, water, methanol, ethanol, alcohols of $C_1$ to $C_{10}$, oxygenates, and the like, and any combination thereof.

The acid catalyst may be any acid catalyst suitable for converting methanol to dimethyl ether. Generally, the acid property of the acid catalyst may be Lewis acidity, Bronsted acidity, or the combination of the both Lewis acidity and Bronsted acidity. Examples of acid catalysts can include, but are not limited to, a zeolite, an ion exchanged zeolite, molecular sieves (e.g., SAPO), metal oxides (e.g., oxides of aluminum, silicon, zirconium, boron, and combinations thereof like alumiosilicates, boroaluminosilicates, borosilicates, and the like), and any combination thereof. Examples of zeolites can include, but are not limited to, MCM-49, HZSM-5-5B, mordenite, ZSM-35, ZSM-48, ZSM-11, Chabazite, boric acid modified alumina, phosphorus oxide modified alumina, ERS-8, MoPOx, and the like, and any combination thereof. Examples of combinations of acid catalyst include, but are not limited to, $WO_3$, $ZrO_2$, $SiO_2$, resins, metal organic frameworks (MOFs), zeolite imidazolate frameworks (ZIFs), and the like, and any combination thereof.

The acid catalyst may have an average diameter (determined by light scattering) of about 1 μm to about 100 μm, or about 1 μm to about 25 μm, or about 20 μm to about 50 μm, or about 25 μm to about 75 μm, or about 50 μm to about 100 μm.

The metal catalyst component may be present in the acid/metal bifunctional catalyst at about 10 wt % or greater (or about 10 wt % to 80 wt %, or 10 wt % to 25 wt %, or 25 wt % to 50 wt %, or 50 wt % to 80 wt %) based on the total weight of the acid/metal bifunctional catalyst. The acid catalyst component may be present in the acid/metal bifunctional catalyst at about 10 wt % or greater (or about 10 wt % to 80 wt %, or 10 wt % to 25 wt %, or 25 wt % to 50 wt %, or 50 wt % to 80 wt %) based on the total weight of the acid/metal bifunctional catalyst. When present, the inert particles may be present in the acid/metal bifunctional catalyst at about 5 wt % or greater (or about 5 wt % to 80 wt %, or 10 wt % to 25 wt %, or 25 wt % to 50 wt %, or 50 wt % to 80 wt %) based on the total weight of the acid/metal bifunctional catalyst system.

A weight ratio of acid catalyst component to metal catalyst component in the acid/metal bifunctional catalyst system can be about 2:1 to about 1:10, or about 1.5:1 to about 1:5, or about 1:1 to about 1:4.

The acidity of the acid/metal bifunctional catalyst system measured with pyridine for Bronsted acid cites (1545 $cm^{-1}$ and 1450 $cm^{-1}$ infrared spectra bands) and ammonia for Lewis acid cites (1620 $cm^{-1}$ and 1450 $cm^{-1}$ infrared spectra bands) may be cumulatively about 1 site to about 250 sites, or 25 sites to 200 sites, or 50 sites to 150 sites.

Direct Synthesis of Dimethyl Ether from Syngas

Figure 2:
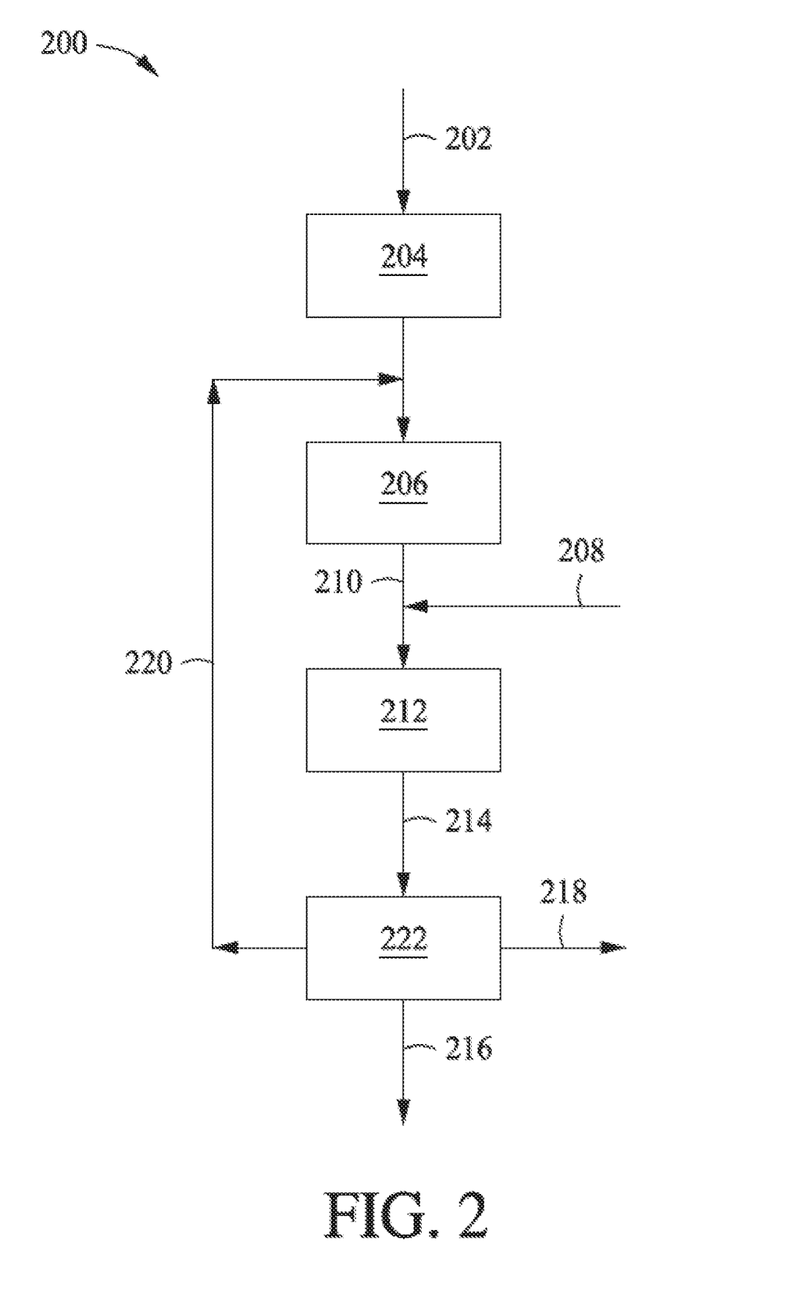
FIG. 2 is a flowchart illustrating an example integrated system and process for producing dimethyl ether from natural gas according to one or more embodiments of the present invention.

An example 200 method and system for the production of dimethyl ether from natural gas is illustrated in FIG. 2. A natural gas stream 202 is fed to a pretreater 204 to remove contaminants such as sulfur, chlorides and olefins. The pretreater 204 may be a single unit or, more likely, it is a series of units for removing the different types of contaminants found in the natural gas stream 204. For example, the pretreater 204 may include a desulfurizing column for removing sulfur. The pretreater 204 can also include a guard bed to remove chlorides and/or a hydrotreater to covert olefins to paraffins.

The pretreated natural gas may then be fed to a reformer 206, which may be a reverse flow reactor, to convert the natural gas to a syngas 210. A recycled $CO_2$ stream 220, which may also include recycled methane, can be fed with the treated natural gas to the reformer 206. It is noted that the pretreated natural gas stream may contain essentially zero $CO_2$ (such as the gas in pipeline gas) or it may have a high $CO_2$ content. Steam may also be added to the reformer 206 to promote the conversion of natural gas to syngas.

Steam 208 and syngas 210 are co-fed to a dimethyl ether reactor 212 to produce a product stream 214, which can include dimethyl ether, carbon dioxide, methane, hydrogen, and other byproducts. The dimethyl ether reactor 212 may operate a temperature of about 200° C. to about 300° C. (or about 230° C. to about 270° C.), a pressure of about 20 bar to about 50 bar (or about 30 bar to about 40 bar), and a gas hourly space velocity (GHSV) of about 1,000 $hr^{-1}$ to about 8,000 $hr^{-1}$ (or about 1,500 $hr^{-1}$ to about 3,000 $hr^{-1}$).

The product stream 214 may be fed to one or more separators 222 to separate the methane, carbon dioxide, and other byproducts 218 from dimethyl ether 216. Methane and carbon dioxide may be recycled back to the reformer 206 via the recycle stream 28. The separation of the products may be accomplished using various separation processes including refrigeration, distillation/fractionation, high-pressure or low-pressure flash separation, or membrane separation.

Prior to running the foregoing method, the acid/metal bifunctional catalyst system may be activated by exposure to hydrogen at elevated temperatures (e.g., about 150° C. to about 350° C., or about 200° C. to about 300° C.).

Direct dimethyl ether synthesis may be performed by converting syngas to methanol (Eq. 1) with the in-situ dehydration of methanol to dimethyl ether (Eq. 3). Advantageously, both reactions can occur in the same reactor such that the methanol is nearly instantaneously dehydrated to dimethyl ether as it is produced. In addition, a water gas shift reaction (Eq. 2) is typically present.

$$CO + 2H_2 \leftrightarrow CH_3OH \quad \Delta H_r = -90.84 \text{ kJ/mole} \qquad \text{(Eq. 1)}$$

$$CO + H_2O \leftrightarrow CO_2 + H_2 \quad \Delta H_r = -41.27 \text{ kJ/mole} \qquad \text{(Eq. 2)}$$

The equilibrium of the methanol reaction (Eq. 1) at high temperatures required to promote kinetics, is reactant favored and limits the overall syngas conversion in a traditional methanol process. However, the disclosed acid/metal bifunctional catalyst system may enable the in-situ dehydration of methanol immediately after it is formed, which maintains the system sufficiently far from equilibrium limitations of Eq. 1 and may improve the per-pass conversion of syngas.

Various by-products can also be produced during the conversion of syngas to methanol (e.g., methane, water, carbon dioxide, formic acid) and the conversion of methanol to dimethyl ether (e.g., acetates, hydrocarbons, methane, water, and coke). Acetates are known to facilitate metal sintering and metal ion-exchange on the acid catalyst that lead to catalyst deactivation.

Because the addition of steam reduces the per-pass selectivity to dimethyl ether by converting some carbon monoxide to carbon dioxide (Eq. 2), the amount of water present in the dimethyl ether reactor would conventionally be limited to the minimal amounts desired to mitigate coke formation. However, it has been found that the addition of steam in the proposed integrated process can be used to control production of $CO_2$ in the dimethyl ether reactor, which can improve the carbon efficiency of the system or process as described in further detail herein. Furthermore, surprisingly, it has been found that co-feeding steam in such quantities can reduce the selectivity towards hydrocarbons and oxygenates, thereby improving the acid/metal bifunctional catalyst system stability.

The total reaction of a system for the synthesis of dimethyl ether (Eq. 4) including the water-gas-shift reaction, methanol synthesis reaction, and dehydration reaction is exothermic.

$$2CH_3OH \leftrightarrow CH_3-O-CH_3 + H_2O \quad \Delta H_r = -21.26 \text{ kJ/mole} \quad (Eq. 3)$$

$$3CO + 3H_2 \leftrightarrow CH_3-O-CH_3 + CO_2 \quad \Delta H_r = -246 \text{ kJ/mole} \quad (Eq. 4)$$

It has been found that carbon efficiency can be improved by controlling feed parameters, particularly the amount of water added to either the reforming reactor or the dimethyl ether reactor. Conventionally, syngas conversion process uses factors like $H_2$:CO ratio or M-value, which is ($H_2$—$CO_2$)/(CO+$CO_2$), to define the ideal feed to the syngas conversion reactor. The numerical value selected for this metric typically reflects the ideal stoichiometry for the desired product reaction. Additionally, the presence of water is typically ignored or treated like an inert.

Water, however, plays a critical role in the integrated process described herein. Water may be added in amounts to leverage the water-gas-shift reaction to co-produce $CO_2$ (as needed to maximize carbon efficiency) in the dimethyl ether reactor. The amount of water added is a function of the syngas composition (namely the amount of CO/$CO_2$/$H_2$/$H_2O$ present in the feed to the dimethyl ether reactor), which is a function of the steam reforming relative to the dry reforming carried out in the syngas reactor.

A preferred feed to the dimethyl ether reactor may be described with a modified M value (Mm) per the following equation.

$$Mm = \frac{H_2 - CO_2 + H_2O}{CO + CO_2 - H_2O}$$

Water may be added to the process in total, either in the syngas reactor for steam reforming or in the dimethyl ether reactor. Independent of how the water is split between the reactors corresponds to a modified M-value of about 1.4 to 1.8 (or 1.5 to 1.7, or 1.6).

Various reforming processes may be employed to produce syngas from such a natural gas feedstream including, but not limited to, partial oxidation, steam methane reforming, autothermal reforming, dry reforming, and the like, and any combination thereof. Preferably, the natural gas stream is reformed using a reverse flow reactor.

Any natural gas feedstream can be reformed into syngas. As used herein, "natural gas" refers to a hydrocarbon feed that is predominantly $C_1$ to $C_4$ hydrocarbons, and it may be predominantly methane. The natural gas feedstream can also include carbon dioxide. For simplicity, examples used herein may make specific reference to methane; however, it should be understood that natural gas feedstreams further comprising $C_2$-$C_4$ hydrocarbons may also be used. General equations for the dry reforming and steam reforming for such hydrocarbons are shown in Eq. 5 and Eq. 6, respectively.

$$C_nH_{2n+1} + CO_2 \rightarrow 2nCO + (n+1)H_2 \quad (Eq. 5)$$

$$C_nH_{2n+1} + H_2O \rightarrow nCO + (2n+1)H_2 \quad (Eq. 6)$$

In order to improve carbon efficiency of the system, it is desirable to provide a feed of natural gas and carbon dioxide to the reverse flow reactor at a natural gas:carbon dioxide molar ratio of about 1:1, such as about 0.8:1 to about 1.1:1. For example, 2 moles of $CO_2$ and 2 moles of methane may produce 4 moles of CO and 4 mole of $H_2$ as shown in Eq. 7.

$$2CO_2 + 2CH_4 \leftrightarrow 4CO + 4H_2 \quad (Eq. 7)$$

If the products of Eq. 5 were then fed to the dimethyl ether reactor with steam as a co-feed, the following products would be produced: 1 mole of dimethyl ether, 2 moles of $CO_2$ and 1 mole of $H_2$ (Eqs. 4 and 2).

The reverse flow reactor for reforming the natural gas to syngas may operate at a temperature of about 300° C. and about 1400° C. (or about 500° C. and about 1000° C.) and a pressure range of about 1 bar and about 100 bar (or about 10 bar to about 50 bar).

The effluent from the dimethyl ether reactor may be separated into dimethyl ether, $CO_2$ (optionally with any unreacted $CH_4$, CO, and/or $H_2$), and other byproducts. Any one or combination of separation processes may be employed to perform such separations including, but not limited to, refrigeration, distillation/fractionation, flash separation and membrane separation. The $CO_2$, $CH_4$, and any unreacted intermediates may be recycled as described herein.

Advantageously, recycle streams having desirable compositions can be obtained from separation processes downstream of the dimethyl ether reactor. These recycle streams can be used to improve the carbon efficiency of the integrated system and/or provide other advantages.

In any embodiment, $CO_2$ and $CH_4$, and optionally CO, recovered downstream of dimethyl ether reactor may be recycled upstream of the syngas generation reactor. The $CO_2$ may be provided in sufficient quantities such that when added to the $CO_2$ native to the natural gas feed will achieve the desired natural gas:carbon dioxide ratio, such as a methane:carbon dioxide molar ratio of about 1:1, such as about 0.9:1.1 to about 1.1:0.9. In some cases, it may be desirable to recycle at least a portion of the $CO_2$ and $CH_4$, and optionally CO and methanol, upstream of the dimethyl ether reactor but downstream of the syngas generator reactor.

Hydrogen may also be recovered from the separation processes and used as fuel. Optionally, at least a portion of the hydrogen can be recycled upstream of the dimethyl ether reactor.

Example Embodiments

A first nonlimiting example embodiment of the present disclosure is a method comprising: mixing two or more metal salts and an aluminum salt in water to produce a metal catalyst precursor solution having a pH of about 2.5 to about 4.0; mixing the metal catalyst precursor solution and a basic solution having a pH of about 10 to about 13 to produce a mixture with a pH of about 6 to about 7 and a precipitate; producing a powder from the precipitate; and calcining the powder to produce a metal catalyst. Optionally, the example embodiment may further include one or more of the following: Element 1: wherein producing the powder from the precipitate comprises: washing the precipitate; drying the precipitate; and grinding the precipitate, wherein the powder comprises 5 wt % or less of the water; Element 2: wherein the metal catalyst precursor solution is at 40° C. to 90° C. when mixing with the basic solution; Element 3: wherein the basic solution comprises sodium carbonate, sodium hydroxide, ammonia hydroxide, ammonia carbonate, sodium hydrogen bicarbonate, and any combination thereof; Element 4: wherein the two or more metal salts comprise a first metal salt that is a salt of a first metal selected from the group consisting of Cu, Cr, Ag, Au, Ru, Rh, Pd, Re, Os, Ir, and Pt and a second metal salt that is a salt of a second metal selected from the group consisting of Ti, V, Cr, Mn, Fe, Co, Ni, Zn, a rare earth metal, a La series metal, and a Y series metal; Element 5: Element 4 and wherein two or more first metal catalysts are included in the metal catalyst precursor solution; Element 6: Element 4 and wherein two or more second metal catalysts are included in the metal catalyst precursor solution; Element 7: wherein the metal catalyst is a M1/M2/Al catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different; Element 8: wherein calcining is performed in air at 200° C. to 400° C.; Element 9: wherein the metal catalyst has an average diameter of 0.01 μm to 10 μm; Element 10: wherein the metal catalyst has a $N_2$ BET surface area according to ASTM D3663-03 (2015) of about 40 $m^2$/g to about 200 $m^2$/g; Element 11: wherein the metal catalyst has an average pore volume according to about 0.01 mL/g to about 0.1 mL/g; Element 12: wherein the metal catalyst has an average pore size according to ASTM D4641-17 of about 15 nm to about 30 nm; Element 13: the method further comprising: dry mixing the metal catalyst with an acid catalyst to produce an acid/metal bifunctional catalyst system; Element 14: the method further comprising: mixing the metal catalyst with an acid catalyst and a binder to form a dough; and extruding the dough to produce an acid/metal bifunctional catalyst system; Element 15: the method further comprising: mixing the metal catalyst with an acid catalyst and a solvent to form a slurry; heating the slurry; and drying the slurry to produce an acid/metal bifunctional catalyst system; Element 16: one of Elements 13-15 and wherein the acid catalyst is selected from the group consisting of a zeolite, an ion exchanged zeolite, a molecular sieve, a metal oxide, and any combination thereof; Element 17: one of Elements 13-15 and wherein the acid catalyst is present at 10 wt % to 80 wt % relative to the total catalyst weight in the acid/metal bifunctional catalyst system; Element 18: one of Elements 13-15 and wherein the acid catalyst is present at 10 wt % to 50 wt % relative to the total catalyst weight in the acid/metal bifunctional catalyst system; Element 19: one of Elements 13-15 and activating the acid/metal bifunctional catalyst system in the presence hydrogen at 150° C. to 350° C.; and reacting the activated acid/metal bifunctional catalyst system with a feedstream comprising hydrogen and carbon monoxide; Element 20: Element 19 and wherein reacting is at a temperature of about 200° C. to about 300° C., a pressure of about 20 bar to about 50 bar, and a gas hourly space velocity (GHSV) of about 1,000 hr-1 to about 8,000 hr-1; and Element 21: Element 19 and wherein the reacting the activated acid/metal bifunctional catalyst system with the feedstream is in the presence of steam. Examples of combinations include, but are not limited one or more of Elements 1-12 in combination with one or more of Elements 13-21; two or more of Elements 1, 2, or 8 in combination; two or more of Elements 1-12 in combination; two or more of Elements 9-12 in combination; Element 4 in combination with Elements 5 and 6; one of Elements 13-15 in combination with one or more of Elements 16-21; and one or more of Elements 1-12 in combination with one of Elements 13-15.

A second nonlimiting example embodiment is an acid/metal bifunctional catalyst system comprising the metal catalyst of the first nonlimiting example embodiment optionally further characterized by one or more of Elements 7, 9, 10, 11, or 12.

A third nonlimiting example embodiment is a metal catalyst produced according to the first nonlimiting example embodiment optionally further including or characterized by one or more of Elements 1-12.

A fourth nonlimiting example embodiment is an acid/metal bifunctional catalyst system produced according to the first nonlimiting example embodiment with Element 13, 14, or 15 and optionally further including or characterized by one or more of remaining of Elements 1-21.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

EXAMPLES

Preparation of 68% CuO/30% ZnO/2% $Al_2O_3$ (Sample 1)

Solution A was prepared by dissolving 27.337 g of cupric nitrate trihydrate, 14.426 g of zinc nitrate hexahydrate, and 2.069 g of aluminum nitrate nonahydrate in 300 g of deionized water. The pH of Solution A measured by pH meter was 3.3. Solution B was prepared by dissolving 18.009 g of sodium carbonate in 300 g of deionized water; the pH of Solution B was 11.7. Solution A was heated in a water-bath with a temperature maintained at 65° C. With magnetic stirring, Solution B was slowly added into Solution A. The addition of Solution B to Solution A was stopped when the pH of the mixture solution reached 6.5. While maintaining the temperature of the slurry at 65° C., the mixture slurry was aged for 1 hour with stirring. The mixture was then cooled down to room temperature.

The mixture was then filtered. The slurry cake was recovered by filtration. The wet cake was washed with distilled water thoroughly. The sample was dried at 120° C.

in air for 16 hours. After grinding, the sample powders were placed in a box furnace. The furnace was ramped from room temperature to 300° C. at a rate of 10° F./min (5.6° C./min) in air. The air flowing rate was set at 5 volume/volume catalyst/minute. The samples were held at 300° C. in air for 3 hours.

Preparation of 68% CuO/30% ZnO/2% $Al_2O_3$ (Sample 2)

Solution C was prepared by dissolving 27.337 g of cupric nitrate trihydrate, 14.426 g of zinc nitrate hexahydrate and 2.069 g of aluminum nitrate nonahydrate in 300 g of deionized water. Solution D was prepared by dissolving 18.009 g of sodium carbonate in 300 g of ionized water. Solution D was heated in a water-bath with temperature maintained at 65° C. With magnetic stirring, Solution C was slowly added into Solution D. The addition of Solution C to Solution D was stopped when the pH of the mixture solution reached at 6.5. While maintaining the temperature of the slurry at 65° C., the mixture slurry was aged for 1 hour with stirring. The power of water-bath was turned off and the mixture slurry was cooled down from 65° C. to room temperature. The slurry cake was recovered by filtration. The wet cake was washed with distilled water thoroughly. The sample was dried at 120° C. in air for 16 hours. After grinding, the sample powders were placed in a box furnace. The furnace was ramped from room temperature to 300° C. at a rate of 10° F./min (5.6° C./min) in air. The air flowing rate inside furnace is set at 5 volume/volume catalyst/minute. The samples were held at 300° C. in air for 3 hours.

Preparation of 68% CuO/30% ZnO/2% $Al_2O_3$ (Sample 3)

Solution E was prepared by dissolving 0.4521 g of sodium aluminate in 1.8166 g of nitric acid, which was then diluted with 20 g of deionized water. The solution was kept stirring until it becomes clear. 0.7824 g of zinc nitrate hexahydrate was added in the mixture solution above. Water was added until the total volume of the Solution E reached 50 mL.

Solution F was prepared by dissolving 52.995 g of sodium carbonate in 400 mL deionized water. Water was added until the total volume of the Solution F reached 500 ml. Solution E was heated in a water-bath with temperature maintained at 65° C. With magnetic stirring, Solution F was slowly added into Solution E. The addition of Solution F to Solution A was stopped when the pH of the mixture solution reached 6.5. The power of water bath was turned off and the mixture slurry was cooled down to room temperature. The slurry cake (the mixed hydroxides of Al and Zn) was recovered by filtration, and the wet cake was washed thoroughly with deionized water.

Solution G was prepared by the following steps. The wet cake (the mixed hydroxides of Al and Zn) above was redispersed in 300 ml deionized water to make a slurry. 27.3372 g of cupric nitrate trihydrate and 13.6439 g of zinc nitrate hexahydrate were added to the slurry. Solution G was heated in a water-bath with temperature maintained at 65° C. With magnetic stirring, Solution F was slowly added into Solution G. The addition of Solution F to Solution G was stopped when the pH of the mixture slurry solution reached 6.5. While maintaining the temperature of the slurry at 65° C., the mixture slurry was aged for 1 hour with stirring. The power of water bath was turned off and the mixture slurry was cooled down to room temperature. The slurry cake was recovered by filtration. The wet cake was washed with distilled water thoroughly. The sample was dried at 120° C. in air for 16 hours. After grinding the sample into fine powders, the sample was placed in a box furnace. The furnace was ramped from room temperature to 300° C. at a rate of 10° F./min (5.6° C./min) in air. The air flowing rate is set at 5 volume/volume catalyst/minute. The samples were held at 300° C. in air for 3 hours.

Preparation of 30% CuO/30% ZnO/10% $Al_2O_3$ (Sample 4)

Solution H was prepared by dissolving 2.412 g of sodium aluminate in 9.690 g of nitric acid, which was then diluted with 40 g of deionized water. The solution was kept stirring until it became clear. 4.173 g of zinc nitrate hexahydrate was added in the mixture solution above. Water was added until the total volume of the Solution H reached 100 mL.

Solution I was prepared by dissolving 52.995 g of sodium carbonate in 400 mL deionized water. Water was added until the total volume of the Solution I reached 500 mL.

Solution H was heated in a water-bath with temperature maintained at 65° C. With magnetic stirring, Solution I was slowly added into Solution H. The addition of Solution I to Solution H was stopped when the pH of the mixture solution reached 6.5. The power of water bath was turned off and the mixture slurry was cooled down to room temperature. The slurry cake (the mixed hydroxides of Al and Zn) was recovered by filtration, and the wet cake was washed thoroughly with deionized water. Solution J was prepared by the following steps. The wet cake (the mixed hydroxides of Al and Zn) above was redispersed in 300 mL of deionized water to make a slurry. 27.337 g of cupric nitrate trihydrate and 12.280 g of zinc nitrate hexahydrate were added to the slurry.

Solution J was heated in a water-bath with temperature maintained at 65° C. With magnetic stirring, Solution I was slowly added into Solution J. The addition of Solution I to Solution J was stopped when the pH of the mixture slurry solution reached 6.5. While maintaining the temperature of the slurry at 65° C., the mixture slurry was aged for 1 hour with stirring. The power of water bath was turned off and the mixture slurry was cooled down to room temperature. The slurry cake was recovered by filtration. The wet cake was washed with distilled water thoroughly. The sample was dried at 120° C. in air for 16 hours. After grinding the sample into fine powders, the sample was placed in a box furnace. The furnace was ramped from room temperature to 300° C. at rate of 10° F./min (5.6° C./min) in air. The air flowing rate is set at 5 volume/volume catalyst/minute. The samples were held at 300° C. in air for 3 hours.

Catalysts Properties

The properties (determined by $N_2$ BET) of the catalysts of Samples 1-4 are provided in Table 1.

TABLE 1

| Sample | Surface Area ($m^2$/g) | Pore Volume (mL/g) | Pore Size (nm) |
|---|---|---|---|
| 1 | 129 | 0.04 | 18.2 |
| 2 | 109 | 0.03 | 17.1 |
| 3 | 21 | 0.05 | 13 |
| 4 | 66 | 0.24 | 13.8 |

Table 1 shows the $N_2$ BET surface areas, pore volumes and pore sizes of Sample 1, Sample 2, Sample 3, and Sample 4. Sample 1 with composition of 68% CuO/30% ZnO/2% $Al_2O_3$ was prepared by addition of sodium carbonate solution into the nitrate solutions of Cu, Al, and Zn maintained at 65° C. The pH of the slurry solution increased from 3.3 to 6.5 as the addition of sodium carbonate solution continued. Sample 1 has surface area of 129 $m^2$/g, pore volume of 0.04 mL/g, and pore size of 18.2 nm. The pore volume is quite small.

Sample 2 with the same composition of 68% CuO/30% ZnO/2% $Al_2O_3$ was prepared by addition of the nitrate solutions of Cu, Al and Zn into sodium carbonate solution maintained at 65° C. The pH of the slurry solution decreased from 11.7 to 6.5 as the addition of the nitrate solutions of Cu, Al and Zn continued. Sample 2 has smaller surface area, pore volume and pore size than Sample 1. Sample 2 has surface area of 109 m$^2$/g, pore volume of 0.03 mL/g, and pore size of 17.1 nm.

Sample 3 has the same composition as Sample 1 and Sample 2. Aluminum precursor compound used in the preparation was sodium aluminate, instead of aluminum nitrate nonahydrate as used in the preparations of Sample 1 and Sample 2. In Sample 3 preparation, there are two precipitation steps. The 1st precipitation was made by addition of sodium carbonate solution into the solutions of sodium aluminate and zinc nitrate to form the precipitates of hydroxides of Zn and Al. The precipitates of the hydroxides of Zn and Al were redispersed into water to make a slurry solution. Cupric nitrate and zinc nitrate were added to the slurry of hydroxides of Zn and Al. Then, the 2nd precipitation was made by the addition of sodium carbonate solution into the slurry solution containing Zn and Al hydroxides, and nitrates of Cu and Zn. The surface area of Sample 3 is only 21 m$^2$/g, which is much smaller than Sample 1 and Sample 2. Most likely, the aluminum hydroxide formed during the 1st precipitation interacts with zinc hydroxide. Therefore, it does not have much freedom to interact with cupric hydroxide during the 2nd precipitation. The dispersion and interaction of Cu and Zn oxides in the Sample 3 with alumina is much weaker than those in Sample 1 and Sample 2, resulting in Cu and Zn agglomerations and smaller sample surface area.

Sample 4 was made similarly as Sample 3. Sample 4 has higher alumina content than Sample 3. It has composition of 60% CuO/30% ZnO/10% Al2O3. The surface area of Sample 4 is 66 m$^2$/g, which is much higher than that of Sample 3, but lower than those in Sample 1 and Sample 2. Even though Sample 4 has much higher alumina content than those in Sample 1 and Sample 2.

Figure 3:
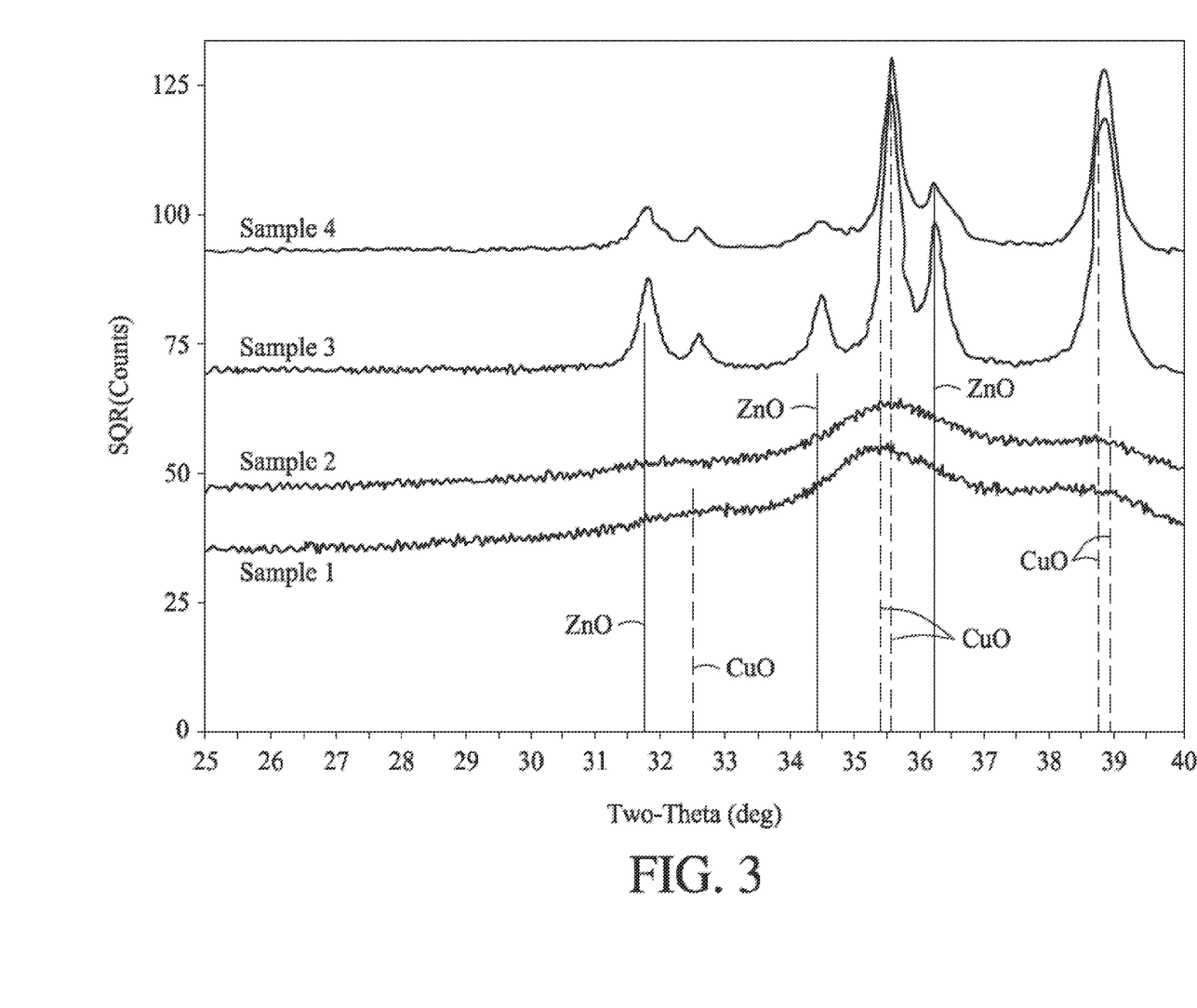
FIG. 3 illustrates the x-ray diffraction (XRD) patterns of various metal catalysts.

FIG. 3 is an X-ray diffraction (XRD) of Samples 1-4. Sample 1 and Sample 2 are amorphous in nature. No crystallized phases were detected. Sample 1 was prepared by the addition of sodium carbonate solution into the nitrate solutions of Cu, Al and Zn. Sample 2 was prepared by the addition of the nitrate solutions of Cu, Al, and Zn into sodium carbonate solution. Inter-formation of the hydroxides of Cu, Al, and Zn by co-precipitations of nitrates of Cu, Al, and Zn with sodium carbonate may interrupt the crystallizations of hydroxides of Cu, Zn and Al. Upon calcination, crystallites of oxides of Cu, Zn, and Al are either amorphous or too small to be detected by XRD. Upon catalyst activation (reduction), Cu metal is highly dispersed on the surfaces of oxides of Zn and Al. In Sample 3 and Sample 4, crystallized phases of CuO and ZnO were detected. Most likely, Al hydroxide formed during the 1st precipitation interacts with Zn hydroxide. It does not have many interactions with Cu and Zn hydroxides during the 2nd precipitation. Therefore, ZnO and CuO were crystallized upon calcination in air at 300° C. After reduction, the dispersions of Cu in the Sample 3 and Sample 4 are much poorer than those in Sample 1 and Sample 2, resulting in Cu particle agglomerations and low CO conversion activities as shown below.

Catalyst Testing

Five catalyst systems were prepared by mixing a reference metal catalyst commercially available CuZnAl catalyst, Sample 1, Sample 2, Sample 3, or Sample 4 with CAT-APAL® Al$_2$O$_3$ with in amounts 50 wt % metal catalyst to 50 wt % acid catalyst. In separate reactions, a reactor was charged with each of the four catalyst systems with 125 μm to 160 μm α-Al$_2$O$_3$ particles above and below the catalyst bed. The catalysts in the reactor were activated by flowing hydrogen at 250° C. over the catalyst bed for 120 minutes. Then, the catalysts were used in a syngas to dimethyl ether reaction under the following conditions: a temperature of 230° C. to 270° C., a pressure of 25 bar to 50 bar, and a gas hourly space velocity (GHSV) of 1,000 hr$^{-1}$ to 8,000 hr$^{-1}$. The reaction feed was 37 vol % to 50 vol % H$_2$, 40 vol % to 50 vol % CO, 13 vol % to 40 vol % CO$_2$, 0 vol % to 3 vol % CH$_4$, 5 vol % to 10 vol % Ar (used as an internal standard), and 0 vol % to 10 vol % of H$_2$O. A gas chromatograph fitted with a flame-ionization detector (FID), a thermal conductivity detector (TCD), and optionally a helium ionization detector (HID) (for low water concentrations of 200 ppm to 2 vol %) was used to analyze the product stream.

Figure 4:
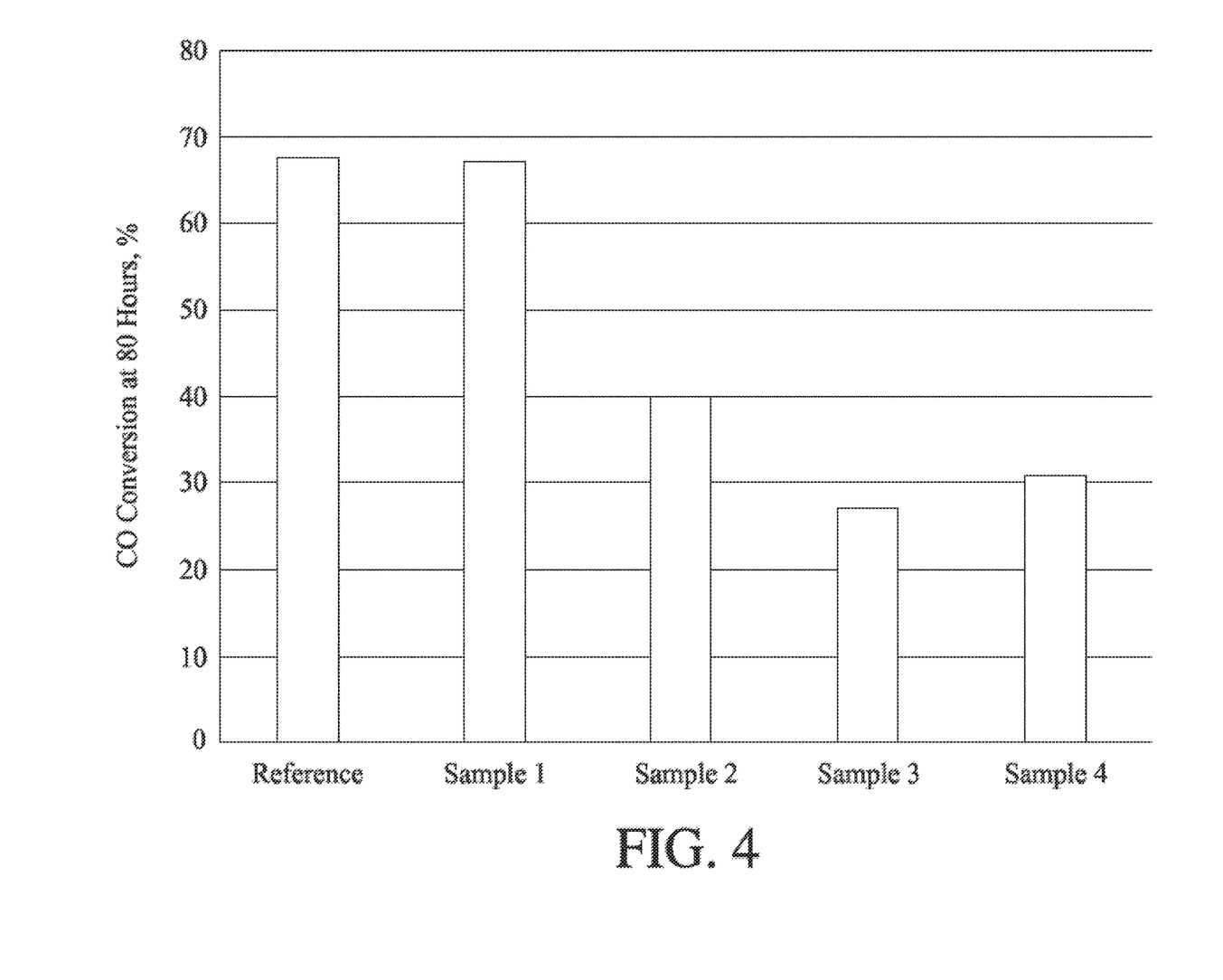
FIG. 4 is a plot of the CO conversion for each of the acid/metal bifunctional catalyst systems based on the Reference and Samples 1-4.

FIG. 4 is a plot of the CO conversion for each of the five catalyst systems after 80 hours of the catalyst beds being exposed to the reaction feed. At 250° C., 35 bar pressure, and GHSV of 2100 hr$^{-1}$, the CO conversion activity of the Reference-based catalyst system reached a steady state, around 70%. The Sample 1-based catalyst system CO conversion activity of 68% is close to that of reference catalyst. Sample 2-based catalyst system has lower CO conversion activity, around 40%. The CO conversion activity results are consistent with the BET surface area data and XRD results. Sample 1 has surface area of 129 m$^2$/g, and Sample 2 has surface area of 109 m$^2$/g, and they are both XRD amorphous. Upon catalyst activation (reduction), Sample 1 catalyst with high surface area has better Cu dispersion on the catalyst surface than Sample 2 catalyst.

The CO conversion activity of Sample 3-based catalyst system is around 27%. It is much lower than those of the Sample 1-based catalyst system and the Sample 2-based catalyst system. Sample 3 has very low surface area of 21 m$^2$/g. Crystallized phases of CuO and ZnO were detected by XRD in Sample 3. After reduction, the dispersion of Cu in Sample 3 is much lower than those in Sample 1 and Sample 2, resulting in low CO conversion activity.

The CO conversion activity of the Sample 4-based catalyst system is around 31%. It is much lower than those of the Sample 1-based catalyst system and the Sample 2-based catalyst system, but slightly higher than then CO conversion activity of the Sample 3-based catalyst system. Sample 4 was made similarly as Sample 3. Sample 4 has higher alumina content than Sample 3. The surface area of Sample 4 is 66 m$^2$/g, which is higher than the surface area of 21 m$^2$/g in Sample 3, but it is still much lower than Sample 1 and Sample 2. Crystallized phases of CuO and ZnO were also detected by XRD in Sample 4.

Figure 5:
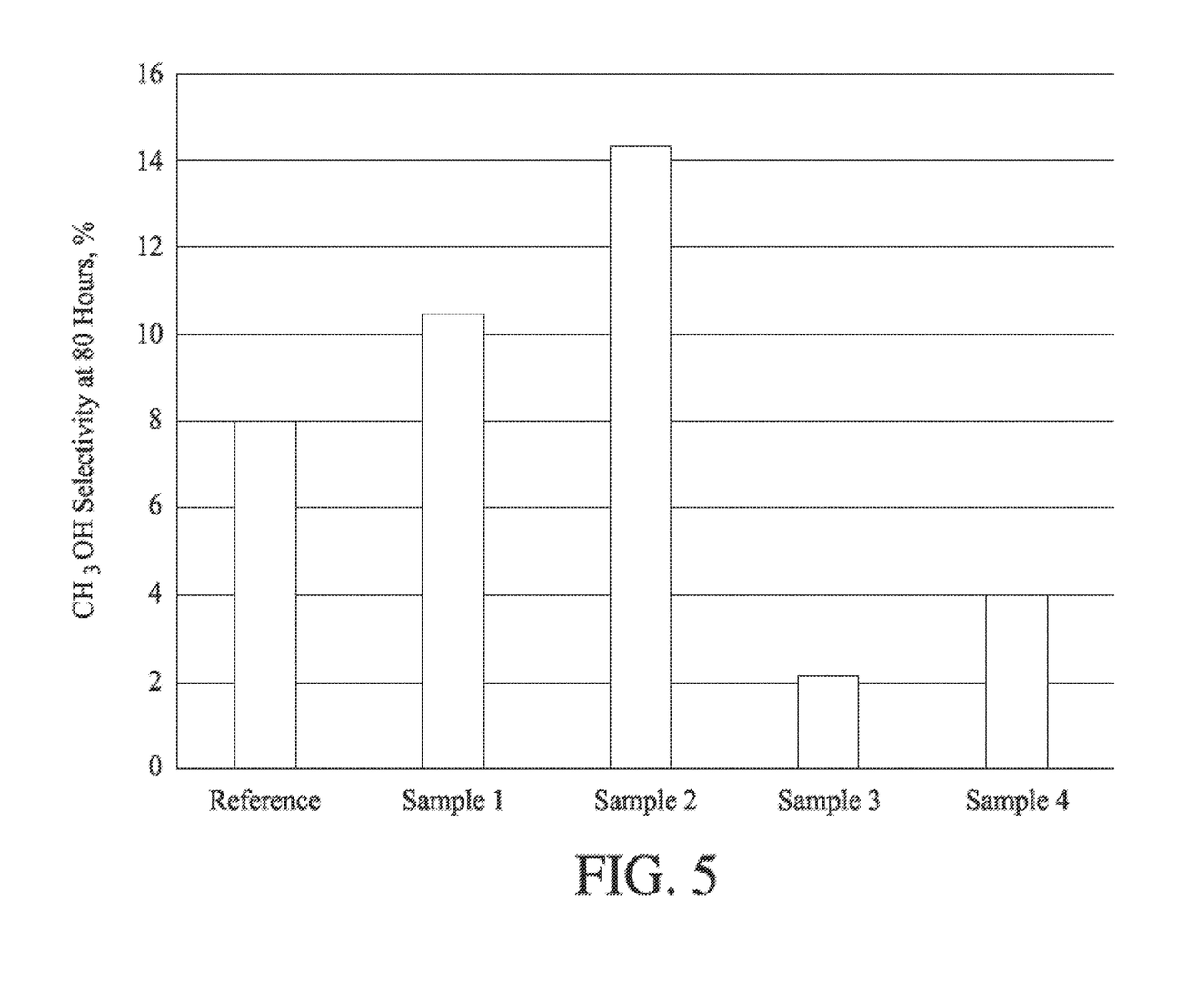
FIG. 5 is a plot of methanol selectivity for each of the acid/metal bifunctional catalyst systems based on the Reference and Samples 1-4.

FIG. 5 is a plot of methanol selectivity for each of the five catalyst systems after 80 hours of the catalyst beds being exposed to the reaction feedstock for 80 hours. Since all CuZnAl samples combine with the same acid catalyst, the dehydration activities in the catalyst systems should be the same, or very close to each other. Therefore, the methanol selectivity is connected to the methanol synthesis activity. Compared to those in the Sample 1-based catalyst system and Sample 2-based catalyst system, the Sample 3-based catalyst system and Sample 4-based catalyst system have much lower methanol selectivites, which is consistent with low CO conversions observed in the Sample 3 and Sample 4.

Figure 6:
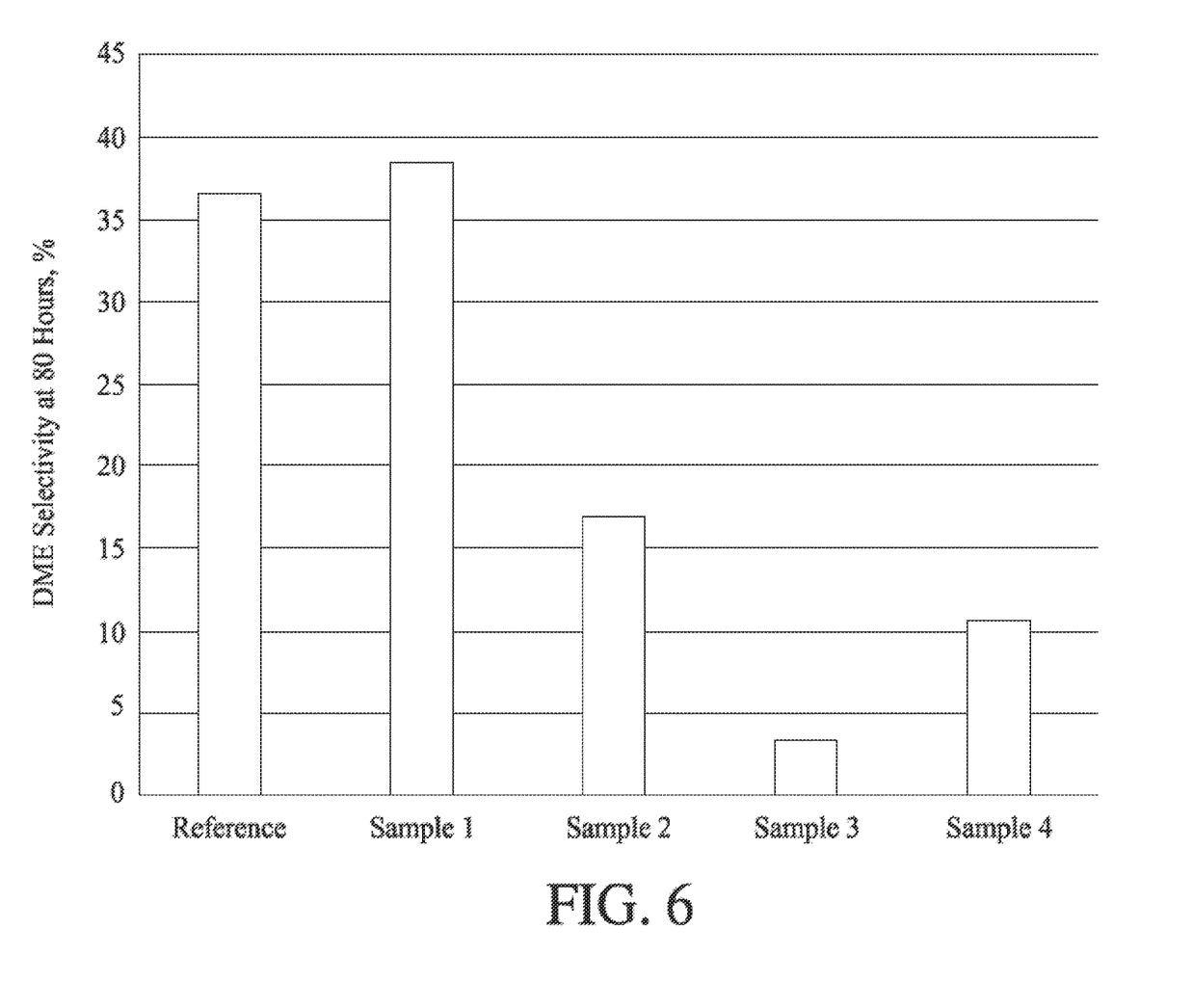
FIG. 6 is a plot of the dimethyl ether selectivity for each of the acid/metal bifunctional catalyst systems based on the Reference and Samples 1-4.

FIG. 6 is a plot of the dimethyl ether (DME) selectivity for each of the five catalyst systems after 80 hours of the catalyst beds being exposed to the reaction feed. The dimethyl ether selectivity of Reference-based catalyst system is 36.5%. Sample 1-based catalyst system has comparable dimethyl ether selectivity around 38.3%, which is higher than the Reference-based catalyst system. Sample 2-based catalyst system has comparable dimethyl ether selectivity around 17%. Sample 3-based catalyst system has comparable dimethyl ether selectivity around 10%.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces.

The invention claimed is:

1. A method comprising:
    mixing two or more metal salts and an aluminum salt in water to produce a metal catalyst precursor solution having a pH of about 2.5 to about 4.0;
    mixing the metal catalyst precursor solution and a basic solution having a pH of about 10 to about 13 to produce a mixture with a pH of about 6 to about 7 and a precipitate;
    producing a powder from the precipitate; and
    calcining the powder to produce a metal catalyst,
    wherein the two or more metal salts comprise a first metal salt that is a salt of a first metal selected from the group consisting of Cu, Cr, Ag, Au, Ru, Rh, Pd, Re, Os, Ir, and Pt and a second metal salt that is a salt of a second metal selected from the group consisting of Ti, V, Cr, Mn, Fe, Co, Ni, Zn, a rare earth metal, a La series metal, and a Y series metal,
    a) wherein two or more first metal catalysts are included in the metal catalyst precursor solution, b) wherein two or more second metal catalysts are included in the metal catalyst precursor solution, or c) a combination of a) and b).

2. The method of claim 1, wherein producing the powder from the precipitate comprises:
    washing the precipitate;
    drying the precipitate; and
    grinding the precipitate, wherein the powder comprises 5 wt % or less of the water.

3. The method of claim 1, wherein the metal catalyst precursor solution is at 40° C. to 90° C. when mixing with the basic solution.

4. The method of claim 1, wherein the basic solution comprises sodium carbonate, sodium hydroxide, ammonia hydroxide, ammonia carbonate, sodium hydrogen bicarbonate, and any combination thereof.

5. The method of claim 1, wherein the metal catalyst is a M1/M2/A1 catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different.

6. The method of claim 1, wherein calcining is performed in air at 200° C. to 400° C.

7. The method of claim 1, wherein the metal catalyst has an average diameter of 0.01 µm to 10 µm.

8. The method of claim 1, wherein the metal catalyst has a $N_2$BET surface area according to ASTM D3663-03 (2015) of about 40 $m^2$/g to about 200 $m^2$/g.

9. The method of claim 1, wherein the metal catalyst has an average pore volume according to about 0.01 mL/g to about 0.1 mL/g.

10. The method of claim 1, wherein the metal catalyst has an average pore size according to ASTM D4641-17 of about 15 nm to about 30 nm.

11. The method of claim 1 further comprising:
    dry mixing the metal catalyst with an acid catalyst to produce an acid/metal bifunctional catalyst system.

12. The method of claim 1 further comprising:
    mixing the metal catalyst with an acid catalyst and a binder to form a dough; and
    extruding the dough to produce an acid/metal bifunctional catalyst system.

13. A method comprising:
    mixing two or more metal salts and an aluminum salt in water to produce a metal catalyst precursor solution having a pH of about 2.5 to about 4.0;
    mixing the metal catalyst precursor solution and a basic solution having a pH of about 10 to about 13 to produce a mixture with a pH of about 6 to about 7 and a precipitate;
    producing a powder from the precipitate; and
    calcining the powder to produce a metal catalyst,
    mixing the metal catalyst with an acid catalyst and a solvent to form a slurry;
    heating the slurry; and
    drying the slurry to produce an acid/metal bifunctional catalyst system.

14. The method of claim 13, wherein the two or more metal salts comprise a first metal salt that is a salt of a first metal selected from the group consisting of Cu, Cr, Ag, Au, Ru, Rh, Pd, Re, Os, Ir, and Pt and a second metal salt that is a salt of a second metal selected from the group consisting of Ti, V, Cr, Mn, Fe, Co, Ni, Zn, a rare earth metal, a La series metal, and a Y series metal.

15. The method of claim 14, a) wherein two or more first metal catalysts are included in the metal catalyst precursor solution, b) wherein two or more second metal catalysts are included in the metal catalyst precursor solution, or c) a combination of a) and b).

16. The method of claim 13, wherein the acid catalyst is selected from the group consisting of a zeolite, an ion exchanged zeolite, a molecular sieve, a metal oxide, and any combination thereof.

17. The method of claim 13, wherein the acid catalyst is present at 10 wt % to 80 wt % relative to the total catalyst weight in the acid/metal bifunctional catalyst system.

18. The method of claim 13, wherein the acid catalyst is present at 10 wt % to 50 wt % relative to the total catalyst weight in the acid/metal bifunctional catalyst system.

19. The method of claim 13, further comprising:
  activating the acid/metal bifunctional catalyst system in the presence of hydrogen at 150° C. to 350° C.; and
  reacting the activated acid/metal bifunctional catalyst system with a feedstream comprising hydrogen and carbon monoxide.

20. The method of claim 19, wherein reacting is at a temperature of about 200° C. to about 300° C., a pressure of about 20 bar to about 50 bar, and a gas hourly space velocity (GHSV) of about 1,000 $hr^{-1}$ to about 8,000 $hr^{-1}$.

21. The method of claim 19, wherein the reacting the activated acid/metal bifunctional catalyst system with the feedstream is in the presence of steam.

22. A method comprising:
  mixing two or more metal salts and an aluminum salt in water to produce a metal catalyst precursor solution having a pH of about 2.5 to about 4.0;
  mixing the metal catalyst precursor solution and a basic solution having a pH of about 10 to about 13 to produce a mixture with a pH of about 6 to about 7 and a precipitate;
  producing a powder from the precipitate; and
  calcining the powder to produce a metal catalyst,
  wherein the metal catalyst has a $N_2$BET surface area according to ASTM D3663-03 (2015) of about 40 $m^2/g$ to about 200 $m^2/g$.

* * * * *

UNITED STATES PATENT AND TRADEMARK OFFICE
CERTIFICATE OF CORRECTION

| | | |
|---|---|---|
| PATENT NO. | : 11,638,912 B2 | Page 1 of 1 |
| APPLICATION NO. | : 16/947699 | |
| DATED | : May 2, 2023 | |
| INVENTOR(S) | : Chuansheng Bai et al. | |

It is certified that error appears in the above-identified patent and that said Letters Patent is hereby corrected as shown below:

On the Title Page

Item (72), Inventors:
Line 3, delete "Jihad M. Daaka," and insert -- Jihad M. Dakka, --.

Signed and Sealed this
Fifth Day of December, 2023

Katherine Kelly Vidal
*Director of the United States Patent and Trademark Office*